United States Patent [19]

Schmid

[11] 4,273,449
[45] Jun. 16, 1981

[54] RADIATION MEASURING APPARATUS

[75] Inventor: Carl J. Schmid, Port Washington, N.Y.

[73] Assignee: Peerless Electronics Research Corp., Westbury, N.Y.

[21] Appl. No.: 15,943

[22] Filed: Feb. 28, 1979

[51] Int. Cl.³ .................... G01N 21/85; G02B 27/14
[52] U.S. Cl. .................... 356/411; 250/204; 350/171; 356/410
[58] Field of Search ............ 356/402, 405–425, 356/432–442, 128–155, 319, 321; 350/171; 250/204

[56] References Cited

U.S. PATENT DOCUMENTS

| | | |
|---|---|---|
| 2,339,053 | 1/1944 | Coleman . |
| 2,692,527 | 10/1954 | Wetzel et al. ............... 356/399 X |
| 2,797,149 | 6/1957 | Skeggs . |
| 2,803,752 | 8/1957 | Warren ............... 356/435 |
| 2,933,293 | 4/1960 | Ferrari . |
| 3,016,800 | 1/1962 | Pliskin . |
| 3,218,908 | 11/1965 | Armington ............... 350/174 |
| 3,342,019 | 10/1967 | Smythe . |
| 3,572,994 | 3/1971 | Hochstrasser . |
| 3,583,813 | 6/1971 | Shibata . |
| 3,599,630 | 8/1971 | Sato et al. ............... 128/6 |
| 3,658,422 | 4/1972 | Wilkinson . |
| 3,746,429 | 7/1973 | Spindel et al. . |
| 4,070,111 | 1/1978 | Harrick . |

FOREIGN PATENT DOCUMENTS 1155846  4/1955  Fed. Rep. of Germany ...... 340/686 X

OTHER PUBLICATIONS

Smith, Warren J., "Modern Optical Engineering", McGraw-Hill, New York 1966, pp. 84–96.

Primary Examiner—John K. Corbin
Assistant Examiner—Bruce Y. Arnold
Attorney, Agent, or Firm—Lee C. Robinson, Jr.

[57] ABSTRACT

A colorimeter in which a beam dividing assembly is supported on a movable carriage intermediate the sample and reference detectors. The assembly separates the incoming collimated light into a sample beam and a reference beam. The movement of the carriage toward or away from the sample produces a decrease or increase in the intensity of the light illuminating the sample and a corresponding increase or decrease in the intensity of the light at the reference detector. The arrangement is such that the apparatus may be readily adjusted to obtain accurate colorimeter readings even for samples having abnormally high or low density characteristics.

14 Claims, 3 Drawing Figures

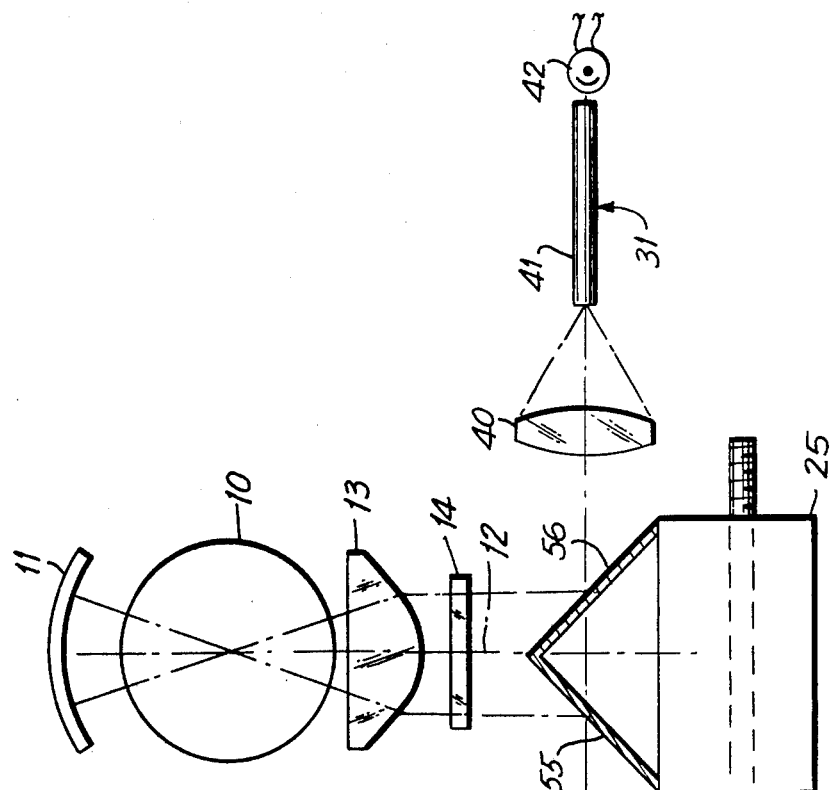
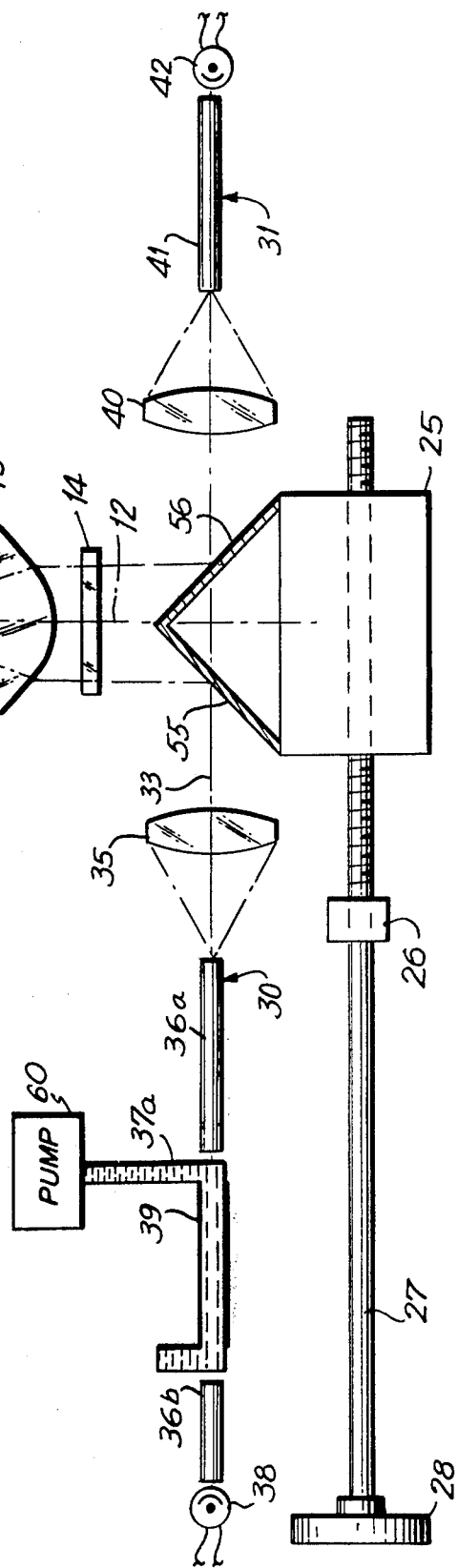

RADIATION MEASURING APPARATUS

BACKGROUND OF THE INVENTION

This invention relates to radiation measuring apparatus and more particularly to apparatus for measuring a particular characteristic of a sample.

The present invention, while of general application, is particularly well suited for use in the quantitative analysis of blood or other body fluids. As is well known, for diagnostic purposes a plurality of samples of body fluid, flowing as serial segments in a stream spaced apart by bubbles of air or other inert fluid, commonly are individually and serially treated with one or more reagents to form a stream having an optical density at a particular wavelength which is indicative of a quantitative characteristic of the sample. In some cases, for example, the reagent comprises an acid solution having a distinct color which reacts with any glucose in the sample to produce a decrease in the density of the color proportional to the amount of glucose. The decrease in density is measured by a colorimeter, and the value is recorded in, say, milligrams of glucose per 100 milliliters of solution.

Heretofore, radiation measuring apparatus of the foregoing type exhibited certain disadvantages. As an illustration, in many such prior apparatus difficulties were encountered in cases in which a particular sample being analyzed exhibited high density and hence reduced the intensity of the radiation to be measured to a level below that at which accurate measurements could be obtained. Variations in the intensity of the radiation source for the apparatus also adversely affected the accuracy of the detected measurements. In addition, and this has been of special moment in cases in which the apparatus was arranged to provide direct readings of the concentration of a substance in the sample, it often was difficult heretofore to calibrate the response of the apparatus so that a given known standard solution resulted in a response at the proper position on the output scale.

SUMMARY

One general object of this invention, therefore, is to provide a new and improved apparatus for measuring radiation representative of a particular characteristic of a sample.

More specifically, it is an object of this invention to provide such radiation measuring apparatus in which accurate measurements are obtained even for samples having abnormally high or low densities.

Another object of the invention is to provide radiation measuring apparatus of the character indicated in which the detected measurements are substantially independent of the intensity of the radiation source.

A further object of the invention is to provide radiation measuring apparatus which may be readily calibrated in accordance with the desired output scale.

Still another object of the invention is to provide radiation measuring apparatus which is economical to manufacture and thoroughly reliable in operation.

In one illustrative embodiment of the invention, the apparatus includes an incandescent lamp or other source of visible or invisible radiation and suitable optics for receiving radiation from the source and directing it along a predetermined path. First and second optical systems are disposed in spaced relationship with each other on opposite sides of the path of radiation. A sample holder, illustratively in the form of a tube containing a continuously flowing sample stream, is located in position to receive radiation from the first optical system. A selected, almost monochromatic portion of the radiation from the source is directed through a radiation dividing assembly, and a part of the radiation then proceeds through the first optical system to the sample in the form of a sample beam. The beam passes through the sample to modify the intensity of the beam in accordance with the optical density of the sample. The intensity of the beam emerging from the sample is detected to produce an output signal representative of the sample density.

In accordance with one feature of the invention, the radiation dividing assembly is supported on a carriage which is movable toward and away from the sample holder to vary the intensity of the radiation reaching the sample. The intensity of the radiation may be readily adjusted with respect to a known standard to provide extremely accurate density measurements even for highly dense or dilute sample materials.

In accordance with another feature of the invention, in certain particularly important embodiments, the radiation dividing assembly serves as a beam divider to separate the received radiation from the source into the sample beam and a reference beam which is detected through the second optical system. The apparatus is provided with first and second detectors for respectively detecting the intensities of these beams, and the signals from the detectors are compared by a ratio detector to produce an output signal which is independent of the intensity of the radiation source.

In accordance with still another feature of several preferred embodiments of the invention, the first and second optical systems are located in optical alignment with each other on opposite sides of the dividing assembly. The movement of the supporting carriage toward and away from the sample holder simultaneously changes the intensities of both the sample beam and the reference beam. As the carriage is moved away from the sample holder, for example, the intensity of the radiation reaching the sample is increased and the intensity of the radiation reaching the reference detector is decreased, while movement of the carriage in the opposite direction decreases the intensity of the radiation sample and increases the intensity of the reference beam radiation. The apparatus may be readily calibrated in accordance with the density of the particular sample being analyzed.

The present invention as well as further objects and features thereof will become more fully apparent from the following detailed description of certain preferred embodiments, when read with reference to the accompanying drawings.

BRIEF DESCRIPTION OF THE DRAWINGS

FIG. 2 is a schematic block diagram of an electrical circuit useful with the apparatus of FIG. 1.

FIG. 3 is a simplified schematic representation of radiation measuring apparatus in accordance with another illustrative embodiment of the invention.

DESCRIPTION OF CERTAIN PREFERRED EMBODIMENTS

Figure 1:
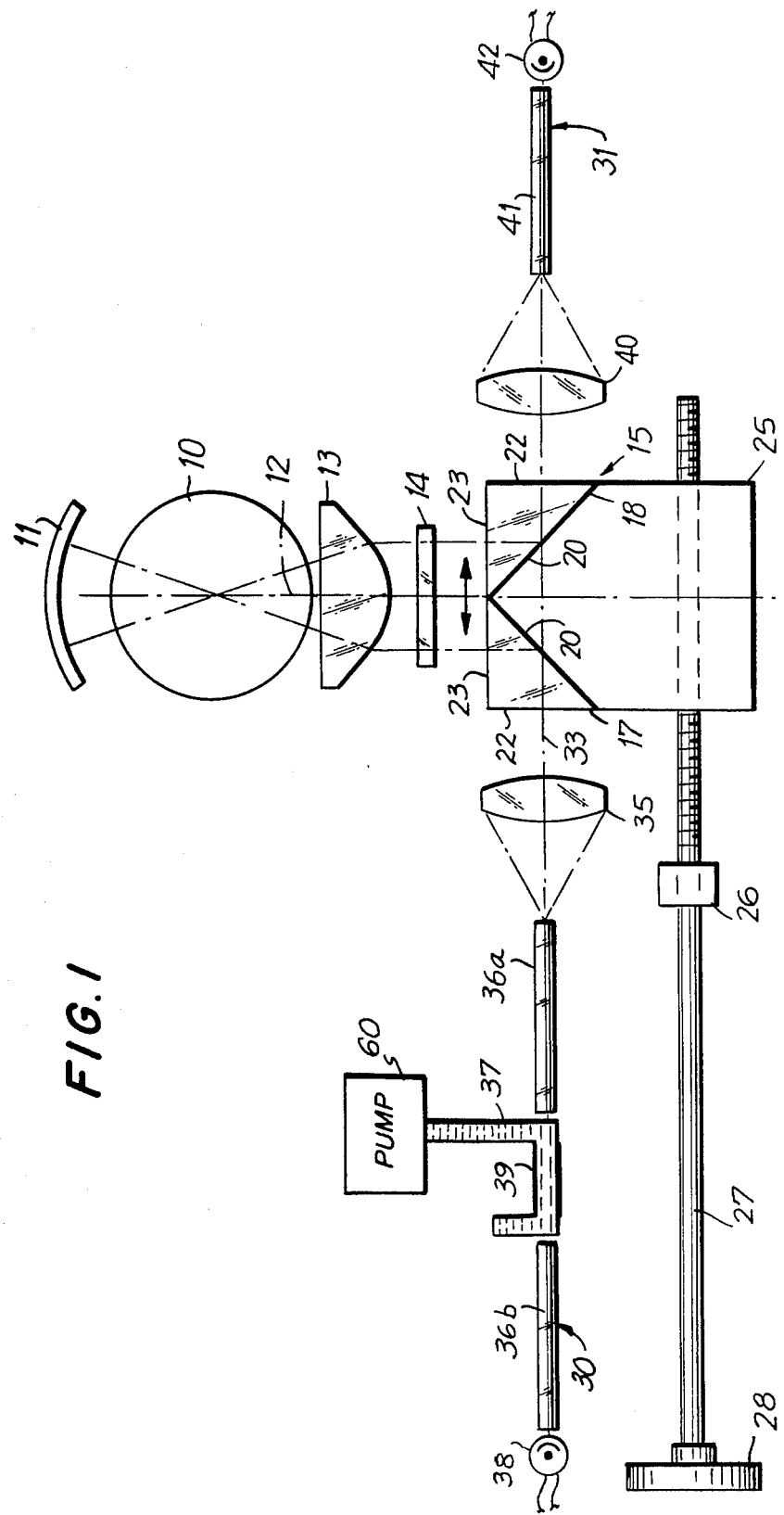
FIG. 1 is a simplified schematic representation of radiation measuring apparatus in accordance with one illustrative embodiment of the invention.

Referring to FIG. 1 of the drawings, there is shown a schematic representation of radiation measuring apparatus in the form of a colorimeter having an incandescent lamp or other suitable light source 10. As used herein, the term "light" includes not only visible light but also radiation having wavelengths longer and shorter than the visible spectrum. Light from the source 10 is collected by a concave mirror 11 and is directed along an optical path indicated generally at 12. The light along the path 12 proceeds through a collimating lens 13 to form parallel rays and then through a band pass filtering lens 14. The lens 14 operates in known manner to permit only a selected, almost monochromatic portion of the light to proceed along the path 12. The band width of the light from the lens 14 illustratively is of the order of fifteen nanometers.

The light from the band pass filter 14 is received by a radiation dividing assembly 15. The assembly 15 includes two right prisms 17 and 18 which each have a diagonal face 20 and two right angle faces 22 and 23. The prisms 17 and 18 are arranged with their faces 22 extending in spaced planes parallel to the optical path 12 and their faces 23 in a single plane perpendicular to the optical path. The diagonal faces 20 are silvered or otherwise provided with a suitable reflective coating, and in the position shown the faces 20 intersect along a line which meets the path 12 at a right angle. With this arrangement, the reflective faces 20 divide the monochromatic light received from the source 10 into two distinct and separate beams, for purposes that will become more fully apparent hereinafter.

The dividing assembly 15 is supported on a movable carriage 25. The carriage 25 is generally in the form of a block of aluminum or other suitable material and is provided with sloping upper surfaces which are cemented to the reflective faces 20 of the prisms 17 and 18, respectively. In the illustrated embodiments the carriage 25 is located behind the optical path 12 to avoid interference with the light along the path.

The carriage 25 is movable in a direction perpendicular to the optical path 12 by means of a calibrated tracking screw 27. The screw 27 extends through a stationary support 26 and a threaded aperture in the carriage and is provided with a knurled knob 28 at one of its ends. By turning the knob 28, the carriage and hence the attached prisms 17 and 18 may be moved as a unit to change the location of the prism assembly relative to the path 12.

A sample optical system 30 and a reference optical system 31 are disposed in spaced relationship with each other on opposite sides of the path 12 in position to receive radiation from the dividing assembly 15. The optical systems 30 and 31 and the dividing assembly 15 are in optical alignment with each other along an optical axis 33 which intersects the path 12 at a right angle.

The sample optical system 30 includes a focusing lens 35 which receives the portion of the monochromatic light reflected by the face 20 of the prism 17. The received light is focused on one end of a tube or light pipe 36a in coaxial relationship with the optical axis 33. The lens 35 forms a sample beam which proceeds through the light pipe 36a and illuminates a sample of material within a tubular sample holder 37. The sample holder 37 is of transparent material but is provided with an opaque coating 39 to prevent the escape of light passing through the sample. As will be understood, the holder 37 is fed by a pump 60 with a continuous stream of liquid sample which has been treated with suitable reagents to produce a particular color characteristic, the density of which is proportional to the amount by weight of a given substance in the sample solution. One illustrative apparatus for supplying the fluid stream to the sample holder is disclosed in the copending patent application Ser. No. 16,161, now U.S. Pat. No. 4,233,001 (issued Nov. 11, 1980), "Peristaltic Pump" by Carl J. Schmid filed concurrently herewith. The intensity of the beam of radiation passing through the sample is reduced as a logarithmic function of the sample density. As the beam emerges from the sample, it passes through a second light pipe 36b and is detected by a photovoltaic cell 38 disposed along the optical axis 33 in juxtaposition with the sample holder.

In a similar manner, the reference optical system 31 receives a reference beam in the form of the portion of the monochromatic light reflected by the face 20 of the prism 18. The reference system 31 includes a focusing lens 40 which focuses the received beam on one end of a light pipe 41. The pipe 41 is axially aligned with the optical axis 33 and serves to direct the incoming light to a photovoltaic cell 42. The intensity of the light detected by the cell 42 is proportional to that of the light source 10 at the selected wavelength.

As best shown in FIG. 2, the sample photocell 38 and the reference photocell 42 are respectively connected to log amplifiers 45 and 46. The output from the amplifiers 45 and 46 is supplied to a ratio detector circuit 49 which compares the amplified signals and produces an output signal representative of the ratio between the detected intensities of the sample and reference beams. The output signal may be recorded by a suitable strip chart recorder 50. The detector 49 and the recorder 50 are calibrated to provide direct readings of the concentration of a selected substance within each of the successive samples moving through the sample tube 37 (FIG. 1) in, say, milligrams per 100 ml. of solution.

As indicated heretofore, the dividing assembly 15 separates the light from the source 10 into substantially monochromatic sample and reference beams having a wavelength determined by the band pass filter 14. The intensities of the sample and reference beams may be simultaneously changed through the use of the knob 28 on the tracking screw 27. If the density of a particular sample within the sample tube 37 is too high to obtain meaningful measurements, for example, the tracking screw 27 is adjusted to move the assembly 15 to the right, as viewed in FIG. 1, away from the sample optical system 30 and toward the reference optical system 31. This movement results in a greater portion of the light from the source 10 being reflected toward the sample system 30 by the prism 17 and a correspondingly lesser portion being reflected toward the reference system 31 by the prism 18. The intensity of the beam illuminating a sample within the sample tube 37 is accordingly increased to provide an increased output signal at the photocell 38, and there is a corresponding decrease in the intensity of the beam reaching the reference photocell 42.

Conversely, in making measurements of very dilute sample materials, the tracking screw 27 is adjusted in a direction to move the dividing assembly 15 away from the reference optical system 31 and toward the sample optical system 30. This latter movement results in a decrease in the intensity of the light illuminating the sample tube 37 and a corresponding increase in the light reaching the reference detector 42. Through the use of a suitable precalibrated scale for the ratio detector 49 and the recorder 50, the response of the apparatus may be readily adjusted such that a given known standard solution falls on the proper place on the scale. The concentration of successive unknown samples may be read directly from the scale without the need for undertaking further calculations.

In a number of good arrangements in accordance with the invention, mirrors are used in place of the prisms in the dividing assembly of the apparatus. Referring to FIG. 3, for example, two flat mirrors 55 and 56 are supported on the carriage 25 for movement as a unit in response to the adjustment of the tracking screw 27. The mirrors 55 and 56 are oriented at right angles to each other in position to direct selected, substantially monochromatic light from the band pass filter 14 in opposite directions along the optical axis 33 through the respective optical systems 30 and 31. The intensities of the resulting sample and reference beams are detected by the photocells 38 and 42 in the manner described heretofore to provide an output signal at the ratio detector 49 and the recorder 50. The position of the mirrors along the axis 33 is readily adjustable thorugh the use of the tracking screw 27 and the knob 28 to divide the received light from the source 10 into sample and reference beams of different intensities. In a manner similar to that described heretofore with respect to the embodiment of FIG. 1, the movement of the mirrors toward or away from the sample optical system 30 produces a decrease or increase in the intensity of the light illuminating the sample and a corresponding increase or decrease in the intensity of the light at the reference detector.

It will be noted from FIG. 3 that the portion of the sample tube 37a along the optical axis 33 is substantially longer than the corresponding portion of the sample tube 37 in FIG. 1. The tube 37a has particular utility in evaluating relatively dilute samples, while the shorter tube 37 is used for samples of higher density. In a given instrument the tubes 37 and 37a are interchangeable, but to obtain readings of high accuracy it is important that the distance between the focusing lens 35 and the photocell 38 remain the same. Accordingly, the lengths of the light pipes 36a and 36b are adjusted in accordance with the particular sample tube being used.

One advantage of the prism arrangement of FIG. 1 over the flat mirror system of FIG. 3 is that the reflective faces 20 of the prisms are protected at all times from scratches and other surface imperfections such as might occur during cleaning, for example.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. In apparatus for measuring a characteristic of a sample, in combination:
    a source of radiation;
    means for receiving radiation from said source and directing the same along a stationary optical path;
    at least one optical system disposed in spaced relationship with said stationary optical path along an axis which intersects said path;
    a sample holder in position to receive radiation from the at least one optical system;
    radiation dividing means located along said stationary optical path at its intersection with said axis for receiving radiation from said source and for dividing the received radiation into separate beams, the dividing means directing one of the beams through said at least one optical system to a sample in said sample holder, said one beam passing through said sample to modify the intensity of said one beam;
    a detector for receiving said one beam from said sample and for detecting the intensity of the received beam;
    a carriage for supporting the radiation dividing means; and
    means for moving said carriage along said axis to similarly move the radiation dividing means and thereby vary the intensity of said one beam, the movement of said carriage along said axis away from said at least one optical system increasing the intensity of the radiation reaching said sample, and the movement of said carriage along said axis toward said optical system decreasing the intensity of the radiation reaching said sample.

2. Apparatus as defined in claim 1, in which said radiation dividing means comprises at least one prism rigidly affixed to said carriage.

3. Apparatus as defined in claim 1, in which said radiation dividing means comprises at least one mirror rigidly affixed to said carriage.

4. In apparatus for measuring a characteristic of a sample, in combination:
    a source of radiation;
    means for receiving radiation from said source and directing the same along a stationary optical path;
    at least one optical system disposed in spaced relationship with said stationary optical path along an axis which intersects said path, said optical system having radiation directing means and means for focusing radiation on the directing means;
    means including a sample of material to be analyzed in position to receive radiation from the at least one optical system;
    radiation dividing means, including at least one prism having a first radiation receiving, surface located perpendicular to said stationary optical path at its intersection with said axis for receiving radiation from said source and a second and third surface, the prism dividing the received radiation into separate beams, said dividing means directing one of said beams through said optical system to said sample, said one beam passing through said sample to modify the intensity of said one beam in accordance with the density of said sample,
    a detector for receiving said one beam from said sample and for detecting the intensity of the received beam;
    a carriage for supporting the radiation dividing means; and
    means for moving said carriage along said axis to similarly move the radiation dividing means and thereby simultaneously vary the intensities of each of said separate beams, the movement of said carriage along said axis away from said optical system increasing the intensity of the radiation reaching said sample, and the movement of said carriage along said axis toward said optical system decreasing the intensity of the radiation reaching said sample.

5. Apparatus for measuring a characteristic of a sample, the apparatus comprising, in combination:
  a source of radiation;
  means for receiving radiation from said source and directing the same along a stationary optical path;
  first and second optical systems disposed in spaced relationship with each other on opposite sides of said stationary optical path along an axis which intersects said path;
  means including a sample of material to be analyzed in position to receive radiation from the first optical system;
  radiation dividing means, including at least one prism having a first radiation receiving, surface located perpendicular to said optical path at its intersection with said axis for receiving radiation from said source and a second and third surface, the prism dividing the received radiation into sample and reference beams, the dividing means directing the sample beam through said first optical system to said sample and directing the reference beam through said second optical system, the sample beam passing through said sample to modify the intensity of said sample beam;
  first and second detectors for respectively receiving the sample and reference beams from said first and said second optical systems and for detecting the intensities of the received beams;
  means connected to said first and second detectors for comparing the intensities of said sample and reference beams;
  a carriage for supporting the radiation dividing means; and
  means for moving said carriage along said axis to similarly move the radiation dividing means and thereby simultaneously change the intensities of both said sample beam and said reference beam.

6. Apparatus for measuring a characteristic of a sample, the apparatus comprising, in combination:
  a source of radiation;
  means for receiving radiation from said source and directing the same along a stationary optical path;
  first and second optical systems disposed in spaced relationship with each other on opposite sides of said stationary optical path along an axis which intersects said path;
  a sample holder in position to receive radiation from the first optical system;
  radiation dividing means including a pair of prisms located along said stationary optical path at its intersection with said axis for receiving radiation from said source and for dividing the received radiation into sample and reference beams, each of said prisms having a radiation receiving surface lying in a single plane perpendicular to said optical path, the dividing means directing the sample beam through said first optical system to said sample holder and directing the reference beam through said second optical system, the sample beam passing through a sample in said sample holder to modify the intensity of said sample beam;
  first and second detectors for respectively receiving the sample and reference beams from said first and said second optical systems and for detecting the intensities of the received beams;
  means connected to said first and second detectors for comparing the intensities of said sample and reference beams;
  a carriage for supporting the radiation dividing means; and
  means for moving said carriage along said axis to similarly move the radiation dividing means and thereby simultaneously change the intensities of both said sample beam and said reference beam, the movement of said carriage in a given direction along said axis increasing the intensity of the radiation reaching said sample and decreasing the intensity of the radiation reaching said second detector.

7. Apparatus as defined in claim 6, in which said axis intersects said stationary optical path at a right angle.

8. Apparatus for measuring a characteristic of a sample, the apparatus comprising, in combination:
  a source of radiation;
  means for receiving radiation from said source and directing the same along a stationary optical path;
  first and second optical systems disposed in spaced relationship with each other on opposite sides of said stationary optical path along an axis which intersects said stationary optical path, said stationary optical path extending along a straight line which is at a right angle to said axis;
  a sample holder in position to receive radiation from the first optical system;
  radiation dividing means located along said stationary optical path at its intersection with said axis for receiving radiation from said source and for dividing the received radiation into sample and reference beams, the dividing means including a first reflective element for directing the sample beam through said first optical system to said sample holder and including a second reflective element in abutting relationship with said first element for directing the reference beam through said second optical system, the sample beam passing through a sample in said sample holder to modify the intensity of said sample beam;
  first and second detectors for respectively receiving the sample and reference beams from said first and said second optical systems and for detecting the intensities of the received beams;
  means connected to said first and second detectors for comparing the intensities of said sample and reference beams;
  a carriage for supporting the radiation dividing means; and
  means for moving said carriage along said axis to similarly move the radiation dividing means and thereby simultaneously change the intensities of both said sample beam and said reference beam, the movement of said carriage along said axis away from said first optical system increasing the intensity of the radiation reaching said second detector, and the movement of said carriage along said axis away from said second optical system decreasing the intensity of the radiation reaching said sample and increasing the intensity of the radiation reaching said second detector.

9. Apparatus as defined in claim 8, which further comprises, in combination:
  collimating means disposed along the stationary optical path for collimating radiation from said source and directing the collimated radiation to said dividing means; and means interposed along said stationary optical path between the collimating means and the dividing means for filtering the collimated radiation.

10. Apparatus as defined in claim 8, in which said abutting reflective elements comprise prisms rigidly affixed to said carriage.

11. Apparatus as defined in claim 8, in which said abutting reflective elements comprise flat mirrors rigidly affixed to said carriage.

12. Apparatus for measuring a characteristic of a sample, the apparatus comprising, in combination:

a source of radiation;

means for receiving radiation from said source and directing the same along a stationary optical path;

means interposed along said optical path for selecting a substantially monochromatic portion of said radiation;

first and second optical systems disposed in spaced relationship with each other on opposite sides of said stationary optical path along an axis which intersects said path, each of said optical systems having radiation directing means and means for focusing radiation on the directing means;

a sample holder in position to receive radiation from the first optical system;

means interposed along said optical path for selecting a substantially monochromatic portion of said radiation;

radiation dividing means located along said stationary optical path at its intersection with said axis for receiving the substantially monochromatic portion of the radiation from said source and for dividing the received radiation into sample and reference beams, the dividing means directing the sample beam through said first optical system to said sample holder and directing the reference beam through said second optical system, the sample beam passing through a sample in said sample holder to modify the intensity of said sample beam in accordance with the density of said sample;

first and second detectors for respectively receiving the sample and reference beams from said sample and said second optical systems and for detecting the intensities of the received beams;

means connected to said first and second detectors for comparing the intensities of said sample and reference beams and for producing an output signal representative of the density of said sample;

a carriage for supporting the radiation dividing means; and means for moving said carriage along said axis to similarly move the radiation dividing means and thereby simultaneously change the intensities of both said sample beam and said reference beam, the movement of said carriage along said axis away from said first optical system increasing the intensity of the radiation reaching said sample and decreasing the intensity of the radiation reaching said second detector, and the movement of said carriage along said axis away from said second optical system decreasing the intensity of the radiation reaching said sample and increasing the intensity of the radiation reaching said second detector.

13. Apparatus for measuring a characteristic of a sample, the apparatus comprising, in combination:

a source of radiation;

means for receiving radiation from said source and directing the same along a stationary optical path;

first and second optical systems disposed in spaced relationship with each other on opposite sides of said stationary optical path along an axis which intersects said path, each of said optical systems having radiation directing means and means for focusing radiation on the directing means;

a sample holder in position to receive radiation from the first optical system;

means for automatically advancing successive samples to be analyzed to the sample holder;

means interposed along said optical path for selecting a substantially monochromatic portion of said radiation;

radiation dividing means located along said stationary optical path at its intersection with said axis for receiving radiation from said source and for dividing the received radiation into sample and reference beams, the dividing means including a pair of right angle prisms in abutting relationship with each other, each of said prisms having a radiation receiving surface lying in a single plane perpendicular to said optical path, said prisms directing the sample beam through said first optical system to said sample holder and directing the reference beam through said second optical system, respectively, the sample beam passing through a sample in said sample holder to modify the intensity of said sample beam in accordance with the density of said sample;

first and second detectors for respectively receiving the sample and reference beams from said first and said second optical systems and for detecting the intensities of the received beams;

means connected to said first and second detectors for comparing the intensities of said sample and reference beams and for producing an output signal representative of the density of said sample;

a carriage for supporting the radiation dividing means; and means for moving said carriage along said axis to similarly move the radiation dividing means and thereby simultaneously change the intensities of both said sample beam and said reference beam, the movement of said carriage along said axis away from said first optical system increasing the intensity of the radiation reaching said sample and decreasing the intensity of the radiation reaching said second detector, and the movement of said carriage along said axis away from said second optical system decreasing the intensity of the radiation reaching said sample and increasing the intensity of the radiation reaching said second detector.

14. Apparatus for measuring a characteristic of a sample, the apparatus comprising, in combination:

a source of radiation;

means for receiving radiation from said source and directing the same along a stationary optical path;

means interposed along said optical path for selecting a substantially monochromatic portion of said radiation;

first and second optical systems disposed in spaced relationship with each other on opposite sides of said stationary optical path along an axis which intersects said path, each of said optical systems having radiation directing means and means for focusing radiation on the directing means;

a sample holder in position to receive radiation from the first optical system;

means for automatically advancing successive samples to be analyzed to the sample holder;

means interposed along said optical path for selecting a substantially monochromatic portion of said radiation;

radiation dividing means including at least one prism having a radiation receiving surface located perpendicular to said stationary optical path at its intersection with said axis, the dividing means receiving the substantially monochromatic portion of the radiation from said source and dividing the received radiation into sample and reference beams, said dividing means directing the sample beam through said first optical system to said sample holder and directing the reference beam through said second optical system, the sample beam passing through a sample in said sample holder to modify the intensity of said sample beam in accordance with the density of said sample;

collimating means disposed along said stationary optical path between said source and said dividing means;

first and second detectors for respectively receiving the sample and reference beams from said first and said second optical systems and for detecting the intensities of the received beams;

means connected to said first and second detectors for comparing the intensities of said sample and reference beams and for producing an output signal representative of the density of said sample;

a carriage for supporting the radiation dividing means; and means for moving said carriage along said axis to similarly move the radiation dividing means and thereby simultaneously change the intensities of both said sample beam and said reference beam, the movement of said carriage along said axis away from said first optical system increasing the intensity of the radiation reaching said sample and decreasing the intensity of the radiation reaching said second detector, and the movement of said carriage along said axis away from said second optical system decreasing the intensity of the radiation reaching said sample and increasing the intensity of the radiation reaching said second detector.

* * * * *